United States Patent [19]

Pike et al.

[11] Patent Number: 4,769,024
[45] Date of Patent: Sep. 6, 1988

[54] REPOSITIONAL ADHESIVE GARMENT CLOSURE TABS AND COMPONENTS THEREFOR

[75] Inventors: Charles O. Pike, Reynoldsburg; Tamela A. Viers, Columbus; Robert R. Zimmerman, Pickerington, all of Ohio

[73] Assignee: Century Adhesives Corp., Columbus, Ohio

[21] Appl. No.: 34,987

[22] Filed: Apr. 6, 1987

[51] Int. Cl.$^4$ ............................................. A61F 13/16
[52] U.S. Cl. .................................................... 604/390
[58] Field of Search ............................... 604/390, 389

[56] References Cited

U.S. PATENT DOCUMENTS

| | | | |
|---|---|---|---|
| 4,576,598 | 3/1986 | Tritsch | 604/390 |
| 4,585,450 | 4/1986 | Rosch et al. | 604/390 |
| 4,650,483 | 3/1987 | Joffe | 604/390 |
| 4,655,761 | 4/1987 | Grube et al. | 604/390 |

Primary Examiner—John D. Yasko
Attorney, Agent, or Firm—Carroll F. Palmer

[57] ABSTRACT

Improved adhesive tabs for fastening disposable garments, e.g., diapers, about the body of a wearer by adhering the tab to an outer portion of the garment made of plastic film of predetermined tensile strength carry a pressure-sensitive adhesive coating having an adhesive strength when plotted as the ordinate against speed of removal from a reference substrate as the abscissa that asymptotically approaches, but does not exceed, the value of the film's predetermined tensile strength whereby the adhesive tab may be repeatedly adhered to and removed from the garment outer portion to fasten and unfasten the garment without tearing its outer portion film. The required adhesive strength property of the adhesive tabs is attached by constructing them to include a backing web, preferably a laminated, multi-layer web, and a first layer of pressure-sensitive adhesive covering one surface of the web, adhering a sheet of non-woven fabric to such first layer on the side thereof opposite to the web and having a second layer of the pressure-sensitive adhesive covering the surface of such sheet opposite to the web so the second layer presents an adhesive surface opposite to the non-woven sheet by which the tab may be adhered to the garment outer portion film.

17 Claims, 2 Drawing Sheets

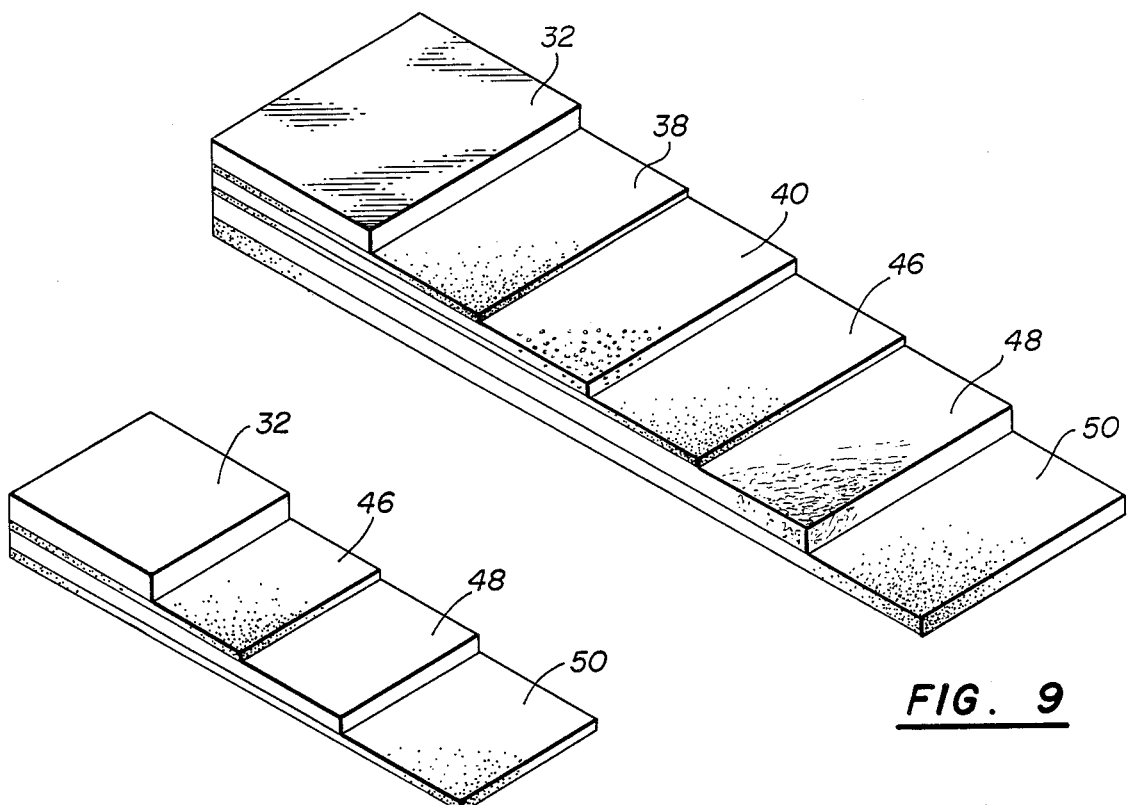
FIG. 9
FIG. 10
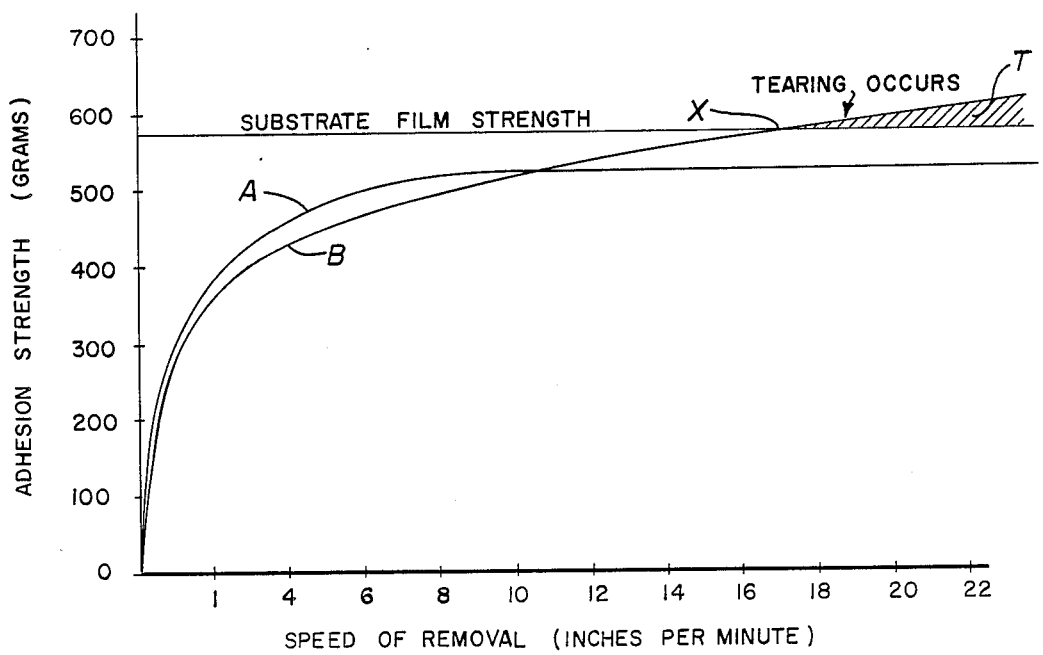
FIG. 11

REPOSITIONAL ADHESIVE GARMENT CLOSURE TABS AND COMPONENTS THEREFOR

BACKGROUND OF THE INVENTION

1. Field of the Invention

This invention relates to disposable garments having unique adhesive fastener tabs and new adhesive products from which to form such fastener tabs.

2. Description of the Prior Art

Disposable garments, e.g., diapers, surgical gowns, bibs, aprons, etc., have become high sales volume items. Hence, much research and development work has been devoted to improving their construction and their methods of manufacture (see U.S. Pat. No. 4,050,462 with reference to diapers). This invention concerns further improvements in disposable garments.

Most all disposable garments, particularly disposable diapers, need to include, as an essential part, some means for fastening the garments about the body of the wearer. The most prevalent fastener means currently used are flexible tabs with a coating of pressure-sensitive adhesive that permits the tab fixed to one part of the garment to secure its free end to another part thereby forming a garment closure. However, such adhesive tab fasteners have presented some problems to which serious attention has been given by manufacturers of the garments.

For disposable diapers to be fully acceptable to purchasers, their fasteners should permit the diaper, once fastened, to be unfastened so the extent of soiling, if any, thereof can be inspected and thereafter refastened if the soiling is not enough to warrant disposal of the diaper. One problem with prior known fastener tabs has been their inability to permit such refastening (called "repositioning"). Thus, in order for the tabs to work properly and not become accidently unfastened, agressive pressure-sensitive adhesives have been used with the tabs. However, when an attempt is made to reposition such tabs, the adhesive does not want to release from the diaper with the result that it becomes torn and must be discarded.

The repositioning problem is increased by the desire of diaper manufacturers to use very thin, liquid-impermeable film as the outer cover material of the diapers. If the diaper is structured so the adhesive tab adheres directly to this outer cover film, the thinner the film, the greater the potential for the diaper to tear when tap repositioning is attempted. Hence, one way to mitigate the tearing problem is to make the outer cover film more robust, i.e., thicker. However, this increases product costs and reduces garment comfort by reducing subtlety.

Other methods of mitigating the repositioning problem is to structure the diapers so that the adhesive surface of the fastener tabs does not adhere directly to the thin outer cover film (see U.S. Pat. No. 4,585,450) or to "toughen" an area of the cover film by some type of treatment (see U.S. Pat. No. 4,643,730). However, these approachs to the problem also increase product costs and limit the areas on the diaper to which the tabs may be repositioned.

In spite of the extensive prior art work expended in improving disposable diapers and other garments, including their fastener tabs (see U.S. Pat. Nos. 4,178,933; 4,227,530 & 4,345,597) a real need exists for a better solution to the fastener tab repositioning problem as discussed above.

OBJECTS

A principal object of the invention is provision of new improvements in disposable garments, particularly disposable diapers.

Further objects include the provision of:

1. Disposable garments having unique adhesive fastener tabs and new adhesive products from which to form such fastener tabs.

2. Pressure-sensitive adhesive fastener tabs for disposable garments which may be fastened directly to thin plastic film outer covers thereof, then removed and reapplied numerous times without losing adhesion or tearing the outer cover film.

3. Such tabs offering possibilities for high-visibility color graphics as a part thereof.

4. Such tabs that are of thin guage possessing excellent flexibility and controlled stretch to accommodate to stresses imposed by movement of parts of the the wearer's body in the closed garment.

5. Fastener tabs for disposable diapers and other garments comprising a pressure-sensitive adhesive structure that exhibits adhesive values that plateau relative to increased speeds of removal of the tabs from the garment portion to which they are fixed in the fastening of the garment.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The stated objects are accomplished, in part, in accordance with the invention by the provision of disposable garments having unique, improved forms of adhesive tabs for fastening the garments about the body of a wearer by adherence of the tabs for such fastening directly to an outer portion of the garment made of thin plastic film of predetermined tensile strength.

The new adhesive tabs are attached at one end to the garment leaving an elongated portion thereof extending from the garment. There is a pressure-sensitive adhesive coating on the elongated portion that has an adhesive strength when plotted as the ordinate against speed of removal from a reference substrate as the abscissa that asymptotically approaches, but does not exceed, the value of the predetermined tensile strength of the garment plastic film, whereby the adhesive tab may be repeatedly adhered to and removed from the garment outer portion to fasten and unfasten the garment without tearing the outer portion of the garment.

The unique adhesive values for the new pressure-sensitive adhesive tabs are attained by particular structuring thereof so that basically they comprise (a) a backing web, (b) a first layer of pressure-sensitive adhesive covering one surface of the web, (c) a sheet of non-woven fabric adhered to such first layer on the side thereof opposite to the web, and (d) a second layer of pressure-sensitive adhesive covering the surface of the sheet opposite to the web so the second layer has an adhesive surface opposite to the non-woven sheet by which the tab may be adhered to the outer cover of the garment.

Preferably, the adhesive tabs comprise (1) a first non-fibrous plastic film having an outer surface and an inner surface, (2) a first layer of adhesive covering the inner surface of the first film, (3) a second non-fibrous plastic film having a first surface and a second surface, the first surface being adhered to the first layer of adhesive, (4) a second layer of adhesive covering the second surface of the second film, (5) a sheet of non-woven fabric adhered to the second layer of adhesive on the side thereof opposite to the second surface, and (6) a third layer of adhesive covering the surface of the non-woven sheet opposite to the second layer of adhesive, such third layer presenting a pressure-sensitive adhesive surface opposite to the non-woven sheet by which the tab may be adhered to the outer portion of the garment. Advantageously, the non-woven sheet is impregnated with the adhesive of the second and third layers.

BRIEF DESCRIPTION OF THE DRAWINGS

A more complete understanding of the invention may be had by reference to the accompanying drawings in which:

FIG. 9 is a fragmentized view of a first embodiment of an adhesive product of the invention designed for use in making adhesive fastener tabs for disposable garments.

FIG. 10 is a view similar to FIG. 9 of a second embodiment of an adhesive product of the invention.

FIG. 11 is a graph comparing adhesive properties of an adhesive product of the invention with a related product of the prior art.

DESCRIPTION OF THE PREFERRED EMBODIMENTS

Figure 1:
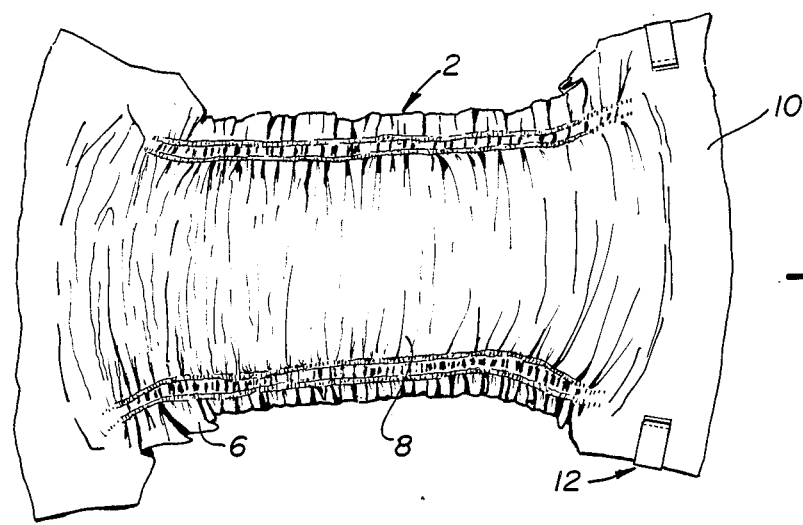
FIG. 1 is perspective view of a disposable diaper constructed in accordance with the invention.

Referring in detail to the drawings, in which identical parts are identically marked, the invention applies generally to disposal diapers or other disposal garments such as surgical gowns, bibs or the like. By way of example, a typical disposable diaper 2 will comprise a liquid-impermeable non-fibrous plastic film outer cover 4, a liquid-permeable inner bodyside liner 6 and an absorbent batt 8 sandwiched between cover 4 and liner 6. The cover 4 and liner 6 are larger than the batt 8 so that marginal portions 10 extend beyond the sides of the batt 8 and the cover and liner are secured together along the end and side marginal portions 10.

A variety of materials are available for use in forming the outer covers, liners and batts in the manufacture of disposable diapers. As previously indicated, the fastener tab repositioning problem depends, in part, on the desire of manufactures to use liquid-impermeable films of plastic, e.g., polypropylene, polyethylene, polyvinyl chloride, etc., that are as thin as possible, e.g., about 1 mil. In any event, the present invention is not dependent upon the precise materials used in the construction of the diapers nor the manner in which they are assembled in the diapers. Hence, the foregoing disclosure about the diapers 2 is illustrative only and this present invention may be used with diapers and other garments of other construction and shapes.

In accordance with this invention, the diaper 2 is provided with improved fastener tabs 12 which are attached by end portion 14 to the diaper marginal portion 10 leaving an elongated portion 16 of tab 12 extending from the diaper 2. The tab portion 16 presents a pressure-sensitive adhesive surface 18 except for its end which is folded back on itself to form an adhesive free finger grip area 20.

Figure 2:
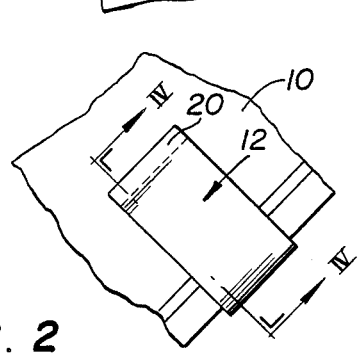
FIG. 2 is a fragmentary perspective view of a portion of the diaper of FIG. 1 which carries one of the new fastener tabs in a "protected" position.
Figure 3:
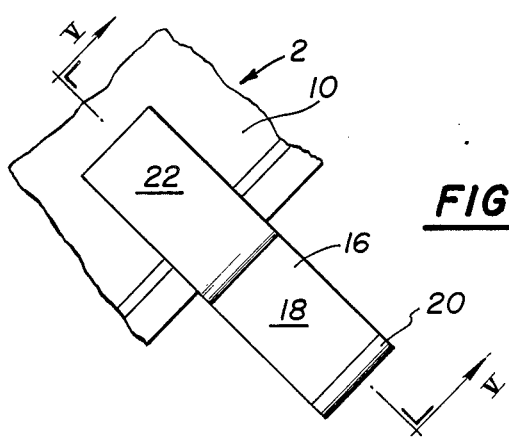
FIG. 3 is a fragmentary perspective view similar to FIG. 2 with the new fastener tab in "opened" position.
Figure 4:
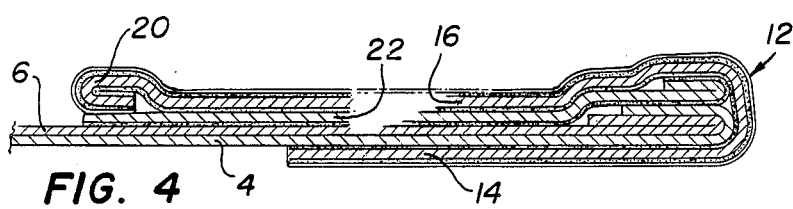
FIG. 4 is a sectional view taken on the line IV—IV of FIG. 2.
Figure 5:
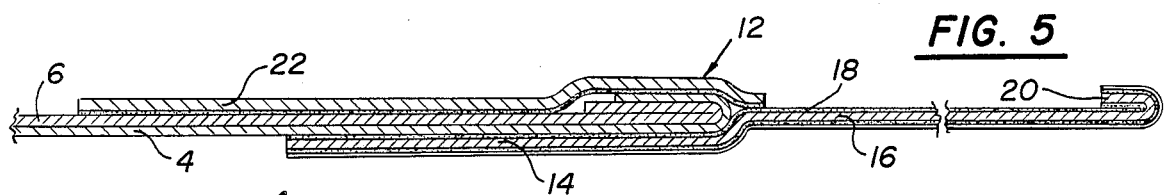
FIG. 5 is a sectional view taken on the line V—V of FIG. 3.
Figure 6:
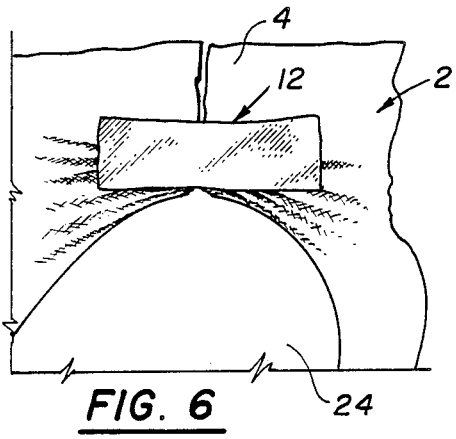
FIG. 6 is a perspective view of the diaper of FIG. 1 fastened on an infant by the new fastener tabs of the invention.
Figure 8:
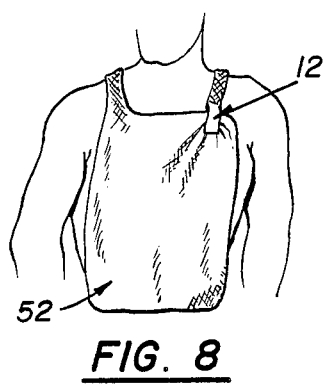
FIG. 8 is a perspective view of a person wearing a bib constructed in accordance with the invention.
Figure 7:
FIG. 7 is a perspective view of a person wearing a surgical garment constructed in accordance with the invention.

On the side opposite to the attached tab end portion 14, a release strip 22 is fixed to the diaper marginal portion 10. This strip 22 is sized to mate with the adhesive surface 18 so that when the tab 12 is folded back over the release strip 22, as shown in FIG. 2, the adhesive surface 18 is in the "protected" position for handling, storage, etc. of the diaper 2. When the diaper 2 is ready to be applied to an infant or other user 24, the tab 12 is removed from the strip 22 and extended from the diaper as shown in FIG. 3. After the diaper has been properly positioned on the user 24, the adhesive surface 18 is contacted directly with the outer cover film 4 of the marginal portion 14 of the diaper 2. In view of the unique structuring of the new fastener tabs 12, the adhesive surface 18 readily "grabs" the cover film 4 to securely fasten the diaper 2 on the user 24. Also, such structuring provides the new tabs 12 with a limited degree of elasticity to that they can stretch to a limited extent to relieve stress on the marginal portions 14 of the diaper 2 and provide more comfort for the user 24.

When it is desired to unfasten the diaper 2 from the user 24, e.g., to inspect amount of soiling, this is easily and safely accomplished with the new fastener tabs 12. Thus, one simply grabs the grip area 20 and pulls the tab 12 away from the cover film 4. As a result of the plateau adhesiveness of the adhesive surface 18, this pulling can be performed at an speed without fear of tearing of the cover film 4. If after inspection, it is found that soiling of the diaper 2 does not warrant removal from the user 24, it can be immediately refastened by repositioning of the fastener tabs 12. This can be done by placing the adhesive surface anywhere on the cover film 4, i.e., it is not necessary, as in many prior art diapers, to replace the tabs 12 only on a preselected area of the diaper 2. Moreover, such fastening and unfastening of the tabs 12 as many time as needed during use of individual diapers without the tabs 12 loosing their aggressive adhesive quality or tearing of the cover film 4.

The appropriate rheological properties of the adhesive surfaces 18 of the new tabs 12 providing the "plateau" effect result from structuring of the unique adhesive products from which the tabs 12 are formed. Such properties include, in addition to the plateau effect, a highly aggressive adhesiveness which enables the adhesive surfaces 18 to "grab" the cover film 4 so that the special steps need not be taken to attain a secure fastening of the tabs 12 to the associated diapers. The aggressiveness of the adhesive surface is measured by the "rolling ball" test of Pressure Sensitive Tape Council, i.e., PSTC—6, in which a metal ball of a given size and weight is allowed to roll down a standard incline and across the adhesive surface. The distance the ball rolls is measured in inches, i.e., the shorter the roll distance and the lower the number, the more "aggressive" the adhesive surface. PSTC 6 values for adhesive surfaces 18 of the invention are between about 1 and 3, as compared to typical values of 10 or greater for prior art adhesive tabs.

The plateau effect property of the unique adhesive surfaces 18 of the invention is illustrated by FIG. 11 wherein (A) the ordinate gives the speed of removal of the adhesive surface of the tab under test at a 120° peel from a flat substrate after having been applied to the substrate with a rolldown weight of 500 grams and (B) the abscissa is the force measured in grams needed to separate the test tab from the substrate at the indicated speed.

Curve A of FIG. 11 is typical adhesive strength values of adhesive surfaces 18 of the new tabs 12 of the present invention. For comparison, curve B is typical of adhesive strength values of adhesive surfaces of prior art adhesive tabs.

In FIG. 11, the horizontal line C gives the tensile strength in grams of a typical non-fibrous plastic film used as a outer cover 4 of a diaper 2, i.e., 1 milpolypropylene film. As shown by the graph of FIG. 11, the adhesive surfaces 18 on the new tabs 12 have an adhesive strength when plotted as the ordinate against speed of removal from a reference substrate as the abscissa that asymptotically approaches, but does not exceed, the value of the predetermined tensile strength strength of the cover film 4 whereby, regardless of the speed with which a tab 12 is pulled from the film cover 4, tearing of the film does not occur. In contrast, curve B of FIG. 11 shows that as speed of removal of the prior art tabs, a point X is reached at which the force needed to pull such tabs from the film exceeds its tensile strength (the shaded area T) and the film tears.

By comparing the results of the rolling ball test and the adhesion strength test on new tabs of the invention and prior art tabs, it can be seen that even though the new tabs "grab" the film of cover 4 much more aggressively than the prior art thereby making fastening of the diapers easier and more certain, the new tabs do not tear the diapers during repositioning.

FIG. 9 discloses one embodiment of an adhesive product 30 of the invention from which fastener tabs 12 can be formed. This product 30 comprises a first non-fibrous plastic film 32 having an outer surface 34 and an inner surface 36, a first layer of adhesive 38 covering the inner surface 36, a second non-fibrous plastic film 40 having a first surface 42 and a second surface 44. Surface 42 is adhered to the adhesive layer 38, a second layer of adhesive 46 covers the second surface 44, a sheet of non-woven fabric 48 is adhered to the adhesive layer 46 on the side thereof opposite to the surface 44, and a third layer of adhesive 50 covers the surface 52 of sheet 48 opposite to the second adhesive layer 46. The third layer presents the pressure-sensitive adhesive surface 18 opposite to sheet 48 and the sheet 48 is impregnated with the adhesive of the second and third layers 46 & 50.

Production of the adhesive product 30 can be preformed on conventional roller coating equipment. The operation starts with the application of the adhesive layer 38 to the film 40 followed, in order, by the steps of (a) lamination of film 32 via layer 38 to film 40, (b) application of adhesive layer 46 to film 40, (c) lamination of sheet 48 via layer 46 to film 40 and (d) application of the adhesive layer 50.

In preferred embodiments, film 40 is opaque while top film 32 is transparent. Film 32 is reverse printed on inner surface 36 with the result that to finished product can be ornamented with impressive graphic designs. The non-woven sheet 48 has been discovered to cooperate with the adhesive layers 46 & 50 to give the unusually high adhesive values as shown by the rolling ball test and at the same time appears to reduce the "leg" of the PS adhesive during removal thereby apparently creating the plateau effect in adhesive strength values. However, this may not be a valid technical explanation of the unique adhesive properties provided by the new adhesive products of the invention so protection of the invention by patent is not intended to rely thereon.

A second embodiment of new adhesive products 52 shown in FIG. 10 has a backing web 54, a first layer 56 of pressure-sensitive adhesive covers inner surface 58 of the web 54, a sheet 60 of non-woven fabric is adhered to the first layer 56 on the side 62 thereof opposite to the web 54, and a second layer 64 of the pressure-sensitive adhesive covers the surface of the sheet 60 opposite to the web 54. The second layer 64 has a pressure-sensitive adhesive surface 18 opposite to the sheet 60 which is impregnated with the pressure-sensitive adhesive of layers 56 & 64.

The products 52 can be produced with equipment and coating operations similar to those indicated for products 30. With all such products, they emerge from the production line as a continuous length of flexible, laminated sheet material only several mils in thickness and in a desired width which is rolled up upon itself around a core to form a roll which can be conveniently handled and stored. To make the tabs 12 of the invention, the sheet material is slit to a width equal to the length of the tab 12 plus the width of the grip area 20. Individual tabs are then sliced transversely therefrom and are applied with automatic machinery in known manner in the assembly of diapers.

By way of specific example of tabs constructed in accordance with the invention:

Film 32 is 0.83 guage cast clear polypropylene film containing a bisamide slip agent and corona treated on surface 36.

Film 40 is 1.5 mil biaxially oriented polypropylene film that has been "voided" to produce opacity.

Sheet 48 is 2.0 mil non-woven fabric formed of nylon fibers, often referred to as nylon scrim.

Adhesive layers 38 & 46 are 0.5 mil thick and layer 50 is 1.0 mil thick. All three layers are formed from the same adhesion composition which is an aqueous emulsion of 99 parts/wt. vinyl acetate/acrylic copolymer adhesive (Flexcrylic 1625 sold by Air Products and Chemicals, Inc.), 1 p/w bisdiamide release agent (W-20 Emulsion sold by Michaelman, Inc.), 0.05 p/w azridine cross-linking agent (CX-100 sold by Polyvinyl Chemical Inc., an ICI group company). The emulsion is adjusted with $NH_4OH$ to pH of 7.0 and the addition of water to give the desired coating viscosity.

As will be apparent to those skilled in the art from the foregoing disclosure, a wide assortment of different materials may be used in place of those recite in the stated specific example, both as to films, sheets and adhesive ingredients. For example, sheets 32, 40 & 52 can be polyethylene, polyvinylchloride, polyvinylidene chloride, glassine paper, etc. Also, sheets 48 & 60 can be formed of celluose fibers, cellulose acetate fibers, polyester fibers, etc. and the guage of the sheets and films may be varied as desired to meet required conditions. Further, while in the specific example, adhesive layers 38, 46 & 50 are all formed from the same emulsion adhesive, each one could be different and could be created from solvent based adhesives rather than emulsion type adhesives. Also, the adhesives may be of the rubber class rather than acrylic class, contain various tackifiers, anti-oxidants, slip agents, anti-blocking agents, and other additives well known to the adhesives art.

The embodiments of the invention in which an exclusive property or privilege is claimed are defined as follows:

1. A flexible laminated sheet product for use in forming pressure-sensitive adhesive tabs for disposable garments having an outer portion formed of plastic film of predetermined tensile strength, which adhesive tabs may be repeatedly adhered to and removed from said outer portion to reposition them for fastening and unfastening said garments about the body of a wearer thereof without tearing said outer portion, said laminated sheet product comprising:
   a first non-fibrous plastic film having an outer surface and an inner surface,
   a first layer of adhesive covering said inner surface of said first film,
   a second non-fibrous plastic film having a first surface and a second surface, said first surface being adhered to said first layer of adhesive,
   a second layer of pressure-sensitive adhesive covering said second surface of said second film,
   a sheet of non-woven fabric adhered to said second layer of adhesive on the side thereof opposite to said second surface, and
   a third layer of said pressure-sensitive adhesive covering the surface of said sheet opposite to said second layer of adhesive, said third layer presenting a pressure-sensitive adhesive surface opposite to said sheet,
   said sheet being impregnated with said pressure-sensitive adhesive of said second and third layers,
   said pressure-sensitive adhesive surface exhibiting an adhesive strength when plotted as the ordinate against speed of removal from a reference substrate as the abscissa that asymptotically approaches, but does not exceed, said predetermined tensile strength value.

2. The sheet product of claim 1 wherein said adhesive of said second layer is the same as the adhesive of said third layer.

3. The sheet product of claim 2 wherein second non-fibrous plastic film is oriented along both the longitudinal axis and the transverse axis thereof.

4. The sheet product of claim 3 wherein said first and second plastic films are formed of polyolefin.

5. The sheet product of claim 13 where said polyolefin is polypropylene.

6. The sheet product of claim 1 wherein said sheet is a non-woven fabric of nylon fibers.

7. The sheet product of claim 1 wherein said pressure-sensitive adhesive surface has a PSTC-6 value of about 3 or less.

8. In a disposable diaper having an outer cover made of plastic film of predetermined tensile strength and an adhesive tab for fastening said diaper about the body of a wearer attached at one end to said diaper leaving an elongated portion thereof extending from said diaper for engagement with said outer cover to effect said fastening, the improvement wherein said adhesive tab comprises:
   a backing web,
   a sheet of non-woven fabric adhered to said backing web, and
   a pressure-sensitive adhesive impregnating and covering said non-woven fabric presenting an adhesive surface that exhibits an adhesive strength when plotted as the ordinate against speed of removal from a reference substrate as the abscissa that asymptotically approaches, but does not exceed, the value of said predetermined tensile strength,
   whereby said adhesive tab may be repeatedly adhered to and removed from said outer cover to reposition it without tearing said outer cover.

9. In a disposable garment having an adhesive tab for fastening said garment about the body of a wearer with an outer portion made of plastic film of predetermined tensile strength to which said adhesive tab is applied for said fastening, said adhesive tab being attached at one end to said garment leaving an elongated portion thereof extending from said garment for engagement with said outer portion to effect said fastening, the improvement wherein said adhesive tab comprises:
   a backing web,
   a sheet of non-woven fabric adhered to said backing web, and
   a pressure-sensitive adhesive impregnating and covering said non-woven fabric presenting an adhesive surface that exhibits an adhesive strength when plotted as the ordinate against speed of removal from a reference substrate as the abscissa that asymptotically approaches, but does not exceed, the value of said predetermined tensile strength,
   whereby said adhesive tab may be repeatedly adhered to and removed from said outer portion to reposition it without tearing said outer portion of said garment.

10. A pressure-sensitive adhesive tab for a disposable garment having an outer cover formed of plastic film of predetermined tensile strength, which adhesive tab may be repeatedly adhered to and removed from said outer cover to reposition it for fastening and unfastening said garment about the body of a wearer thereof without tearing said outer cover, said adhesive tab comprising:
   a backing web,
   a sheet of non-woven fabric adhered to said backing web, and
   a pressure-sensitive adhesive impregnating and covering said non-woven fabric presenting an adhesive surface that exhibits an adhesive strength when plotted as the ordinate against speed of removal from a reference substrate as the abscissa that asymptotically approaches, but does not exceed, the value of said predetermined tensile strength,
   whereby said adhesive tab may be repeatedly adhered to and removed from said outer portion to reposition it without tearing said outer portion of said garment.

11. A pressure-sensitive adhesive tab for a disposable diaper having an outer cover formed of plastic film of predetermined tensile strength, which adhesive tab may be repeatedly adhered to and removed from said outer cover to reposition it for fastening and unfastening said diaper about the body of a wearer thereof without tearing said outer cover, said adhesive tab comprising:
- a backing web,
- a first layer of pressure-sensitive adhesive covering one surface of said web,
- a sheet of non-woven fabric adhered to said first layer on the side thereof opposite to said web, and
- a second layer of said pressure-sensitive adhesive covering the surface of said non-woven fabric opposite to said web, said second layer having an adhesive surface opposite to said sheet by which said tab may be adhered to said outer cover,
- said pressure-sensitive adhesive impregnating and covering said non-woven fabric and said adhesive surface exhibits an adhesive strength when plotted as the ordinate against speed of removal from a reference substrate as the abscissa that asymptotically approaches, but does not exceed, the value of said predetermined tensile strength,
- whereby said adhesive tab may be repeatedly adhered to and removed from said outer cover to reposition it without tearing said outer cover.

12. A pressure-sensitive adhesive tab for a disposable garment having an outer portion formed of plastic film of predetermined tensile strength, which adhesive tab may be repeatedly adhered to and removed from said outer portion to reposition it for fastening and unfastening said garment about the body of a wearer thereof without tearing said outer portion, said adhesive tab comprising:
- a first non-fibrous plastic film having an outer surface and an inner surface,
- a first layer of adhesive covering said inner surface of said first film,
- a second non-fibrous plastic film having a first surface and a second surface, said first surface being adhered to said first layer of adhesive,
- a second layer of adhesive covering said second surface of said second film,
- a sheet of non-woven fabric adhered to said second layer of adhesive on the side thereof opposite to said second surface, and
- a third layer of adhesive covering the surface of said sheet opposite to said second layer of adhesive, said third layer presenting a pressure-sensitive adhesive surface opposite to said sheet of non-woven fabric by which said tab may be adhered to said outer portion of said garment,
- said sheet of non-woven fabric being impregnated with said adhesive of said second and third layers and said pressure-sensitive adhesive surface exhibits an adhesive strength when plotted as the ordinate against speed of removal from a reference substrate as the abscissa that asymptotically approaches, but does not exceed, the value of said predetermined tensile strength,
- whereby said adhesive tab may be repeatedly adhered to and removed from said outer cover to reposition it without tearing said outer cover.

13. The adhesive tab of claim 12 wherein said adhesive of said second layer is pressure-sensitive and is the same as the adhesive of said third layer.

14. The adhesive tab of claim 13 wherein second non-fibrous plastic film is oriented along both the longitudinal axis and the transverse axis thereof.

15. The adhesive tab of claim 14 wherein said first and second plastic films are formed of polyolefin.

16. The adhesive tab of claim 15 where said polyolefin is polypropylene.

17. The adhesive tab of claim 12 wherein said sheet is a non-woven fabric of nylon fibers.

* * * * *